(12) United States Patent
Bildersee et al.

(10) Patent No.: US 11,404,162 B1
(45) Date of Patent: Aug. 2, 2022

(54) PREDICATE-GATED OPERATION OF MEDICALLY RELATED DEVICES

(71) Applicant: Verily Life Sciences LLC, South San Francisco, CA (US)

(72) Inventors: Adam Bildersee, Burlingame, CA (US); Brett Schleicher, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 404 days.

(21) Appl. No.: 16/740,142

(22) Filed: Jan. 10, 2020

Related U.S. Application Data

(60) Provisional application No. 62/791,155, filed on Jan. 11, 2019.

(51) Int. Cl.
| | | |
|---|---|---|
| *G16H 40/40* | (2018.01) | |
| *G16H 20/10* | (2018.01) | |
| *G16H 40/67* | (2018.01) | |
| *G16H 10/60* | (2018.01) | |
| *A61B 5/00* | (2006.01) | |
| *G16H 80/00* | (2018.01) | |

(52) U.S. Cl.
CPC ........... *G16H 40/40* (2018.01); *A61B 5/0022* (2013.01); *A61B 5/746* (2013.01); *G16H 10/60* (2018.01); *G16H 20/10* (2018.01); *G16H 40/67* (2018.01); *G16H 80/00* (2018.01)

(58) Field of Classification Search
CPC ........ G16H 40/40; G16H 10/60; G16H 20/10; G16H 40/67; G16H 80/00; A61B 5/0022; A61B 5/746
See application file for complete search history.

(56) References Cited

U.S. PATENT DOCUMENTS

| 4,869,392 | A | * | 9/1989 | Moulding, Jr. | ........ | A61J 7/0481 |
| | | | | | | 221/241 |
| 2012/0179488 | A1* | | 7/2012 | Tanimoto | ............. | G06Q 10/087 |
| | | | | | | 705/2 |

FOREIGN PATENT DOCUMENTS

JP     2009-215340     *    9/2009

OTHER PUBLICATIONS

Lee, Iris. "Can Timer Cap put a lid on opioid epidemic? Moorpark firm finds abuse prevention market for a convenience product." San Fernando Valley Business Journal 22.17: 7(1). CBJ, L.P. (Aug. 21, 2017) (Year: 2017).*

* cited by examiner

*Primary Examiner* — Linh Giang Le
(74) *Attorney, Agent, or Firm* — Kilpatrick Townsend & Stockton LLP

(57) ABSTRACT

Techniques are disclosed for gating state transitions of a medically related device. Specifically, detection that a particular condition is satisfied can directly or indirectly trigger switching the medically related device from operating in a normal operation mode to a suppressed operation mode.

20 Claims, 2 Drawing Sheets

PREDICATE-GATED OPERATION OF MEDICALLY RELATED DEVICES

CROSS REFERENCE TO RELATED APPLICATIONS

This application claims the benefit of U.S. Provisional Patent Application No. 62/791,155 entitled "Predicate-Gated Operation Of Medically Related Devices" filed Jan. 11, 2019, which is hereby incorporated by reference in its entirety for all purposes.

BACKGROUND

Various medically related actions are now frequently performed outside medical facilities. For example, many medications are administered by patients themselves (e.g., via oral, inhalation, or injection administration). As specific illustrations, an epipen, inhaler, or implant may be configured to release medication, or medication can may be provided in oral or injectable form. As another example, devices or kits can be used to monitor patient health states, such as an indication as to a glucose level, whether a particular bacteria is present, etc.

However, the use of devices risks the possibility that the devices may be misused and/or that patients may use the devices without following recommended actions. In these instances, patients may experience undesirable effects due to (for example) sub-optimal medication administration or sub-optimal interpretation of analysis results.

SUMMARY

In some embodiments, a computer-implemented method is provided. The method can include accessing a usage protocol for a medically related device. The usage protocol can identify one or more operation characteristics that are to control an operation of the medically related device when a particular condition is satisfied. The one or more operation characteristics can correspond to a suppressed state of operation of the medically related device as compared to a normal state of operation of the medically related device. The method can also include collecting data that corresponds to a usage characteristic of the medically related device, a medically related state of a person, environmental data indicating a presence or characteristic of an object near the medically related device, and/or account data of the person. The method can further include determining, based on the collected data, that the condition is satisfied. The method can still further include, in response to determining that the condition is satisfied: causing the medically related device to operate in accordance with the one or more operation characteristics and to enter the suppressed state of operation; and causing an alert to be presented at a user device. The alert can include an indication that the medically related device is operating in the suppressed state and/or a characterization of the collected data.

In some embodiments, computer-program product is provided. The computer-program product can be tangibly embodied in a non-transitory machine-readable storage medium. The computer-program product can include instructions configured to cause one or more data processors to perform part or all of one or more methods disclosed herein.

In some embodiments, a system is provided. The system can include one or more data processors and a non-transitory computer readable storage medium containing instructions which, when executed on the one or more data processors, cause the one or more data processors to perform part or all of one or more methods disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

DESCRIPTION

Figure 1:
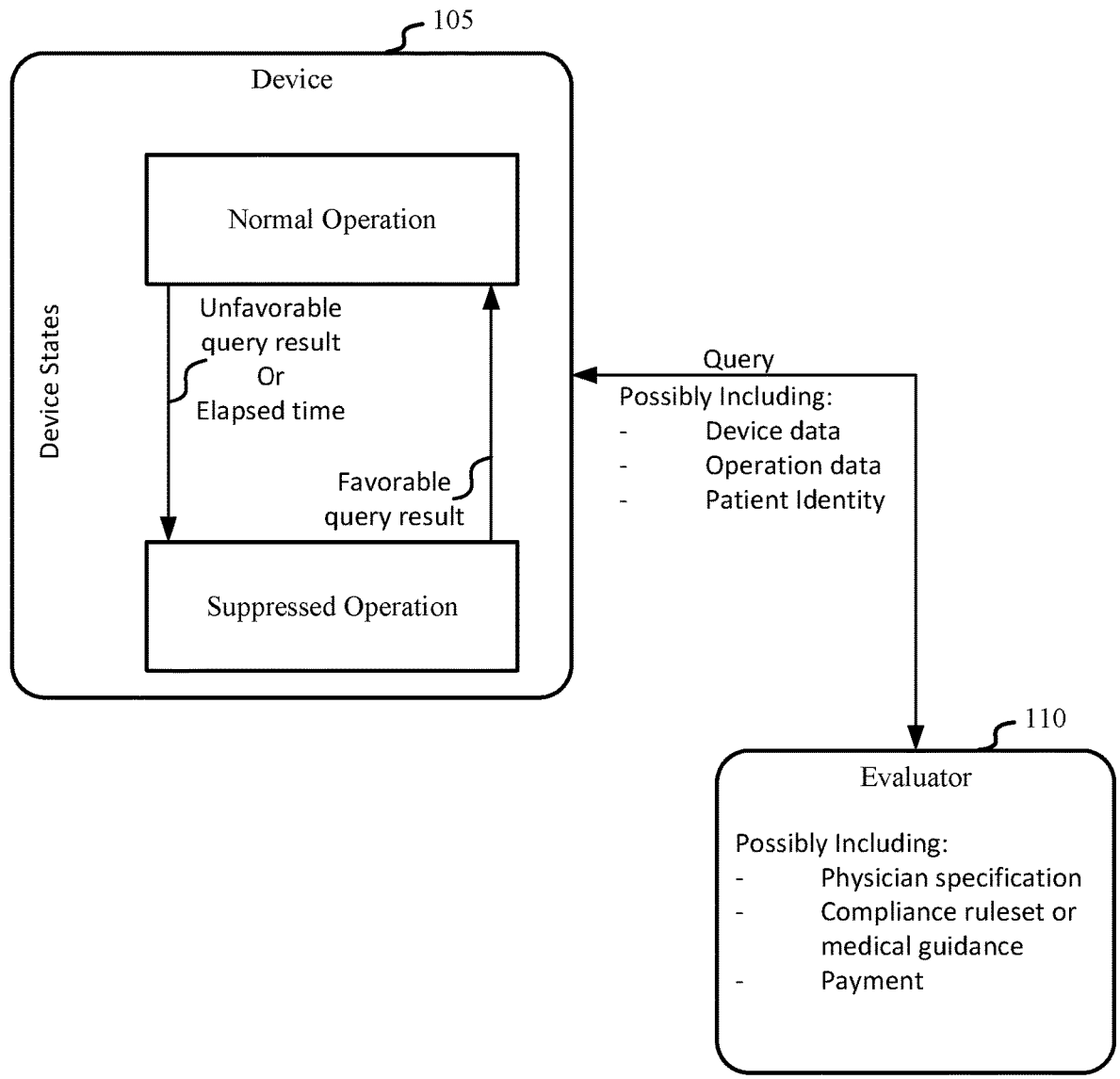
FIG. 1 illustrates an interaction between a medically related device and an evaluator device.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

In some instances, a smart medically related device is provided. An operation of the smart device can be controllable such that a normal operation can be suppressed upon determining that a particular condition is satisfied. Thus, a normal operation of a device or medication can be blocked or prevented in response to an indication that an external authority and/or predicate is unsatisfied. The suppressed operation may have an effect of (for example) preventing access to a medication, reducing an amount of medication made accessible or administered, preventing a presentation of a result of an analysis of a biological sample, etc.

The particular condition can be configured such that its satisfaction depends on (for example) whether a device is being used in accordance with a protocol, whether a potentially dangerous environmental data point is detected, whether a user is abiding with a defined medical-professional-consulting protocol, whether a particular medical data point (e.g., vital sign and/or blood pressure) has been collected (e.g., using the medically related device, received at the device from another device at which the medical data point was collected or received at the medically related device via user input), whether one or more sensors and/or user input indicates that a user participated in at least a threshold time and/or intensity of exercise, whether data collected at the smart medically related device (e.g., collected via one or more sensors or a user interface) or received at the smart medically related device (e.g., from another device) indicates that a medical test (e.g., pulmonary function test and/or spirometry) was completed, whether data collected at the smart medically related device (e.g., collected via one or more sensors or a user interface) indicates that a task (e.g., breathing exercise or portion of an eating plan) was completed, whether data collected at or received at the smart medically related device indicates that one or more rehabilitation programs or one or more administration protocols of one or more other medications are being complied with, and/or whether particular information (e.g., payment authorization or survey responses) has been provided by a user. Controlling the device's operation in this manner can thus enable a device or medication to be provided even when unrestricted access to the device or medication may pose a high risk (e.g., to the patient's health or an authority's priorities).

The determination as to whether the condition is satisfied and/or causing suppression of the device's operation can be performed at (for example) the medically related device, at a controller device (e.g., smart phone wirelessly communicating with the medically related device), or a remote server. An alert may also be presented at the medically related device and/or one or more other devices (e.g., the controller device, a device of a physician or a device of a pharmacist). In some instances, receipt of an instruction from an authorized device (e.g., a device of a physician, pharmacist or medical facility associated with a patient) to resume normal operation can cause the medically related device to return (at least temporarily) to normal operation.

Thus, the medically related device can regulate its operation based on whether a defined condition is satisfied. In some instances, the condition is assessed at regular intervals, and the device can transition to a suppressed state upon determining that any suppression condition is satisfied or that at least a threshold number of suppression conditions are satisfied. A condition may then be configured to delay a transition to a suppressed state by a time delta of the regular intervals. In some instances, a transition to a suppressed state can be postponed indefinitely so long as the condition is repeatedly satisfied. In some instances, the transition can only be postponed up to a threshold number of times. Upon reaching the threshold, a new state-transition condition may be effected. For example, the new state-transition condition may indicate that the device is to enter the suppressed state or cannot transition from the suppressed state to a normal state until a signal is received from another authorized device that indicates that the user (for example) called or visited a physician.

Upon determining that the condition is satisfied, the operation may change from a normal state to a suppressed state (e.g., reducing an intensity or frequency of a performed function or preventing performance of the function). This change (e.g., along with an alert presented at the medically related device or at an associated controller device) may have an effect of encouraging a patient to perform an action that causes the condition to no longer be satisfied and/or that causes another condition (e.g., that, when satisfied, causes an operation to revert to a normal state) to be satisfied. An independent authority (e.g., physician, medical provider or pharmacist) can be alerted of the condition satisfaction, and an instruction from the independent authority can have an effect of preventing the medically related device from entering the suppressed state, defining the suppressed state or causing the medically related device to return to the normal state. The device thereby operates to require or encourage compliance with one or more rules (e.g., for treatment follow-up, for clinical-trial follow-up, for payment, for dosing constraints, etc.).

FIG. 1 illustrates an interaction between a medically related device (a controllable device 105) and an evaluator (e.g., controlling) device 110 and/or evaluator entity. Controllable device 105 can include (for example) an epipen, inhaler, prescription bottle, medical test kit, medical implant configured to deliver medication doses, medical implant configured to deliver electric-stimulation treatments, auto-injector (e.g., subcutaneous auto-injector) for administering injectable medications, pill or medication dispensing appliance, pill organizer with multiple (e.g., individually) locking container wells, and/or a device used in phototherapy, transcutaneous electrical nerve stimulation (TENS), transcranial magnetic stimulation (TMS), thermal therapy, or oxygen therapy.

Controllable device 105 can be configured to operate in one of at least two states. The at least two states include a normal operation and a suppressed operation. The normal operation can include (for example) operating so as to provide access to a medication, treatment or information. The suppressed operation can include (for example) operating to prevent access to the medication, treatment or information or operating to provide a lower quantity or different type of the medication, treatment or information relative to that provided in the normal operation.

The state in which controllable device 105 operates can depend on a query result. The query result can be pushed from evaluator device 110 to controllable device 105 or pulled from evaluator device 110 by controllable device 105. In some instances, controllable device 105 transmits a notification (e.g., of a condition being met and/or of a detected request for access at the device for information, treatment or medication), which may trigger evaluator device 110 to provide an interface to receive input that triggers a push communication. For example, controllable device 105 can transmit a query to evaluator device 110 that includes a patient identifier, operation data (e.g., indicating that the device has transitioned into a suppressed-operation state) and device data (e.g., identifying a number of treatments provided or availed within a defined time period). The query may trigger evaluator device 110 to present an interface that includes a field to receive an instruction to resume operation in the normal-operation state.

The query result may include (for example) an indication as to in which state controllable device 105 is to operate, for how long controllable device 105 is to operate in a given state, and/or parameters of an operation in a given state. For example, a favorable query result may indicate that controllable device 105 is to operate in a normal-operation state for a single additional treatment dose or defined period of time.

The state in which controllable device 105 operates can also or alternatively depend on satisfaction of one or more conditions. For example, the state may transition from normal operation to suppressed operation when a clock has reached a time threshold. The clock may be configured to be reset in response to a defined type of communication (e.g., indicating that an appointment with a physician has occurred).

Thus, satisfaction of a condition may directly and automatically affect an operation state of controllable device 105, and/or it may trigger at least part of a communication exchange (e.g., with evaluator device 110) that may potentially affect an operation state of controllable device 105. As further examples, the condition may be configured to be satisfied upon detecting at least a predefined activity pattern based on signals from one or more sensors in controllable device 105 and/or upon detecting that usage of controllable device 105 (e.g., in terms of a count of doses or treatment or summed dosage or intensity) has met a predefined threshold. In some instances, the condition may be configured to be satisfied upon detecting a particular type of pharmacy data (e.g., upon automatically detecting or receiving a signal that indicates that a medication that is stored at controllable device 105 is expired, that a prescription that corresponds to controllable device 105 or user thereof has changed, that a refill is due, that a medication that is stored at controllable device 105 is no longer supplied, has been recalled and/or is no longer covered by insurance on file in association with controllable device 105 (or a user thereof).

In some instances, controllable device 105 includes a user interface to receive inputs and/or output outputs. For example, the user interface can include a keyboard, touchscreen, display, speakers and/or microphone. An output component of the user interface can present information (for example) continuously, at regular times, periodically, in response to detecting a particular event (e.g., satisfaction of a condition, release of medication, etc.) and/or upon detecting a request for the information. The information may include (for example) a summary of operation parameters (e.g., X uses per Y time), progress towards a usage threshold (e.g., nth dose release of Y total doses before lockout), and/or an alert when a lockout is being approached (e.g., one month of out six months remaining before reset is required by physician). The information can include an estimated time of (a current or potentially future) lock out and/or estimated time of normal operation (e.g., until lockout or upon transitioning back to normal operation).

A medically related device can include (for example) an independent device or an implantable device. The medically related device can be configured to perform one or more medically related functions independently and/or based on one or more communications from one or more other devices. For example, the medically-related device may be configured to unlock a medication canister at designated times (e.g., in accordance with a dosing regimen), to release medication at designated times (e.g., in accordance with a dosing regimen) or to perform an analysis of a biological sample.

The medically related device can be configured to connect (e.g., wirelessly connect) with one or more other devices. For example, the medically related device can communicate via a short-range connection (e.g., Bluetooth or Bluetooth Low Energy) with a nearby controller device (e.g., a smart phone, tablet or computer). The communication may be mediated by specialized software (e.g., an app) installed on the controller device. For example, upon receiving an instruction, the controller device may initiate a discover process to identify the medically related device as being nearby, such that future communications can be appropriately processed.

The controller device may be configured to connect (e.g., wirelessly connect) with one or more remote devices. For example, the controller device may communicate via WiFi with a remote server or cloud computer. The remote server or cloud computer may be configured to communicate (e.g., via WiFi) with one or more other devices, such as a server, computer, smart phone or tablet associated with a medical entity (e.g., a physician, pharmacist, medical facility, etc.).

The network can, in some instances, facilitate distributed processing. For example, the remote server can be used to identify a particular condition to be effected at the medically related device. As another example, the medically related device can collect data to be assessed using the condition, and the condition assessment can be performed at the controller device. As another example, the remote server may be used to verify permissions to determine whether an instruction to revert to normal operation is received from an entity or device that is authorized to provide the instruction for the medically related device.

In some instances, an emergency-access condition can further be defined in addition to one or more particular conditions. The emergency-access condition can be configured to trigger a transition from the suppressed state to the normal state or to a modified normal state even when the particular condition is not satisfied. The emergency-access condition can be configured to be satisfied upon detecting user input at the medically related device that corresponds to a request to trigger emergency-access operation of the medically related device or upon receiving a signal from another device that corresponds to authorization to transition to emergency-access operation of the medically related device. In some instances, A modified normal state may (for example) permit access to up to a predefined number of medication dosages (in accordance with a dosing regimen), up to a predefined number of treatment instances, and/or may correspond to a normal-state operation but only for a predefined time period.

In some instances, detecting that the emergency-access condition has been satisfied can trigger a transmission of an alert (e.g., to a device of an evaluator, physician and/or pharmacist). The alert can identify the medically related device, a patient corresponding to the medically related device, a date and time at which the emergency-access condition was satisfied, and/or an identification of the normal state or modified normal state in which the medically related device is operating. The alert may be accompanied with an option configured to, upon selection, cause a control communication to be transmitted to the medically related device that triggers the medically related device to change its operation (e.g., to a suppressed state or to an unmodified normal state).

In some instances, one or more emergency-access conditions can be configured to correspond to different tiers of conditions and condition-satisfaction triggers. For example, an emergency-access condition may be configured to trigger a transition to different modified normal states (e.g., that provide access to a medication or therapy for a different number or duration of times) depending on a number of times that the emergency-access condition was satisfied within a predefined time window. As another example, different emergency-access conditions can be defined to trigger a transition to a same (normal or modified normal) state or different states. The different emergency-access conditions can be configured to be escalating, such that (for example) a second emergency-access condition that is assessed after one or more first emergency-access conditions were satisfied requires receipt of an increasing number of requests to grant emergency access (from multiple devices), requires a health-related reading to be recorded at or received at the device (that was not required by the one or more first emergency-access conditions), etc. Escalating emergency-access conditions may further trigger escalating alerts. For example, in response to satisfaction of escalated alerts, a same alert or different alerts may be transmitted to an increased number of devices, an increase amount of information may be included in transmitted, and/or an increased urgency indication may be included in or associated with the alert.

Figure 2:
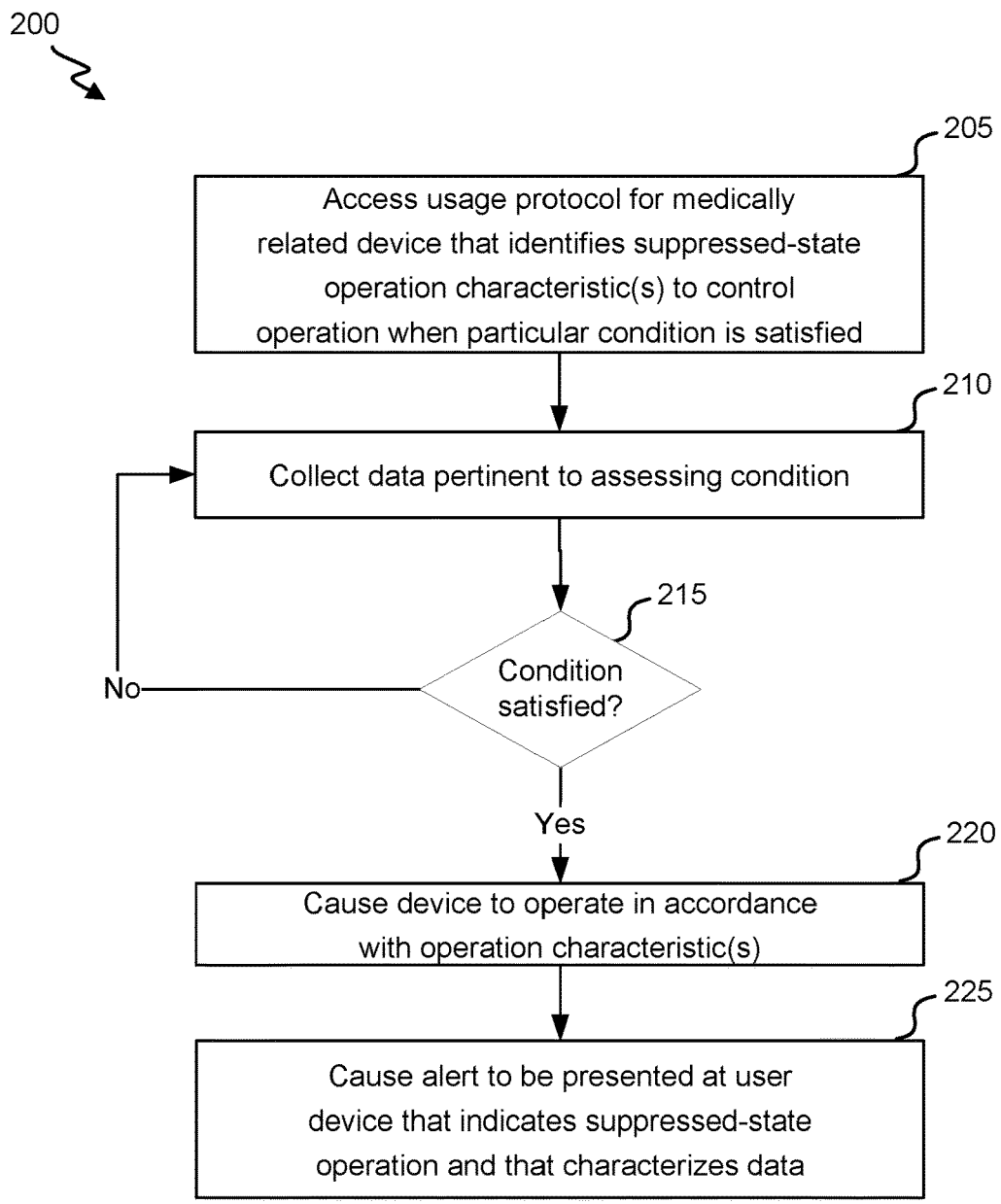
FIG. 2 illustrates a flowchart for a process of controlling the operation of a medically related device.

FIG. 2 illustrate a flowchart for a process 200 of controlling the operation of a medically related device according to an embodiment of the invention. Process 200 begins at block 205 where a usage protocol for a medically related device is accessed. The usage protocol can identify one or more suppressed-state operation characteristics to at least partly control operation of the medically related device when a particular condition is satisfied.

At block 210, data pertinent to assessing the particular condition is collected. The data can correspond to (for example) a usage characteristic of the medically related device (e.g., a number of times the device has been used to deliver a medication or treatment within a predefined time period; a frequency at which the device has been used to deliver a medication or treatment across a predefined time period; a time since a last use during which the device was used to deliver a medication or treatment; an average, cumulative or last dosage of a medication delivered via the device across a predefined time period; or an average, median, mode or cumulative intensity of a treatment delivered via the device across a predefined time period). The data can correspond to a medically related state of a person (e.g., as identified via input received at the device or as communicated from another device or as identified by processing one or more measurements collected by one or more sensors of the device). The data can include environmental data indicating a presence or characteristic of an object near the medically related device and/or account data of the person.

At block 215, it is determined, based on the collected data, whether the particular condition is satisfied. When it is determined that the particular condition is not satisfied, process 200 can return to block 210. When it is determined that the particular condition is satisfied, process 200 continues to block 220 where the medically related device is caused to operate in accordance with the one or more operation characteristics.

At block 225, an alert is caused to be presented at a user device (e.g., an evaluator device, physician device, pharmacist device and/or patient device). The alert can indicate that the medically related device is operating in the suppressed state and/or can characterize (e.g., include and/or summarize) the data that was sufficient for the condition to have been satisfied.

In some instances, another condition can then be assessed to determine whether to cause the device to transition back from the suppressed state to the normal state. For example, the other condition may be configured to be satisfied upon detecting that a predefined period of time has elapsed since the transition from normal state to suppressed state (or since another time), that an instruction signal has been received from another device that indicates that normal operation is to be resumed, etc.

EXAMPLES

Example 1—Implanted Device with Automated-Dosing Function. An implanted device can be configured to administer a treatment in accordance with a defined protocol. The treatment administration may include, for example, electrically stimulating a biological structure (e.g., nerve or brain region) or releasing a medication.

A condition set for the device may include that the patient must have had a patient with a medical provider in accordance with a defined schedule in order for the treatment to be administered in accordance with the defined protocol. In this instance, the condition indicates that the patient is to see a physician at least once every six months in order for the device to operate normally. When it is detected that it has been five months from a last appointment, a notification may be presented at a smart phone alerting the patient that there is one month left in the six-month period and that the patient must have an appointment with a physician within the next month to have the device operate normally.

If the patient has the appointment within the six-month period, a remote server may receive an instruction communication from a physician device that corresponds to an instruction to reset a clock for the time period. The remote server may communicate (e.g., via a controller device) with the implanted device to effect the instruction.

If the six-month period expires without a notification of the appointment having occurred, the implanted device may detect the expiration and send a first alert communication (e.g., indicative of the expiration and including a device identifier) to the remote server (e.g., via the controller device). The remote server can generate and transmit a second alert communication (e.g., indicative of the expiration and including a device or patient identifier) to a physician device (e.g., associated with the implanted device. The second alert communication may include one or more instruction options configured to receive instruction indicating how the implanted device is to operate (e.g., in a normal state, in a normal state for a defined period of time, to administer a different type of treatment or to cease administering treatment). A second default state (e.g., administering a reduced-intensity or lower frequency treatment or ceasing treatment) can be identified and implemented if no contrary instruction is received.

The controller device may also generate and present a notification that indicates that the time period has expired and identifies the new operation state. Thus, the notification and/or the new treatment state may encourage the patient to comply with the recommended follow-up regiment.

Example 2—Inhaler Device with Medication-Access Function. An inhaler device can be configured to release a medication (e.g., a short-acting beta2-agonist) upon activation (e.g., depression of a top of a canister in the inhaler). A condition set for the device may include that the medication be administered no more frequently than a defined frequency threshold (e.g., no more than 24 times per 24-hour time period).

In response to detecting each activation, the inhaler device can determine whether the threshold has been met and can log a time of the activation (e.g., and whether medication was delivered). The determination can be made (for example) by comparing a current count of activations to the threshold. The current count may be reset and/or adjusted (e.g., to exclude representations of old medication administrations) in accordance with a data-maintenance protocol. When the threshold has not been met, the medication can be released and the count can be incremented.

When the threshold has been met, the inhaler device can lock, such that the medication is not released (or such that medication is not subsequently released for a given time period). Further, the inhaler device can send an alert communication to an associated controller device (e.g., smart phone), which can present a notification that the allotted usage has been exceeded and can send a communication to the remote server (e.g., corresponding to an indication that the device has been locked, including usage data and including an identifier of a patient or device). The remote server can send a communication to a device associated with a physician that can include the usage data and identifier of the patient.

An interface presented at the physician device can display the usage data and patient identifier and can include one or more options to specify how the inhaler device is to operate (e.g., whether it is to remain locked, a period of time for which it is to remain locked, whether it is to unlock in accordance with one or more specified parameters, or whether it is to unlock).

Example 3—Pill Bottle with Medication-Access Function. A pill bottle device can be configured to contain medication in the form of pills. Specifically, the pill bottle device can include a canister to include the pills and a locking mechanism can be configured such that the canister can only be opened when the locking mechanism is disengaged. The pill bottle device can include electronics such that the locking mechanism is disengaged in accordance with a dosing schedule (e.g., such that it disengages every 8 hours until the device is opened).

A condition set for the device may be configured to be satisfied upon detecting a nearby pill bottle that is associated with an identifier of another medication that may trigger an undesired interaction with the medication. The pill bottle device includes a code reader (e.g., RFID reader) or transmitter that can detect data from any of one or more nearby pill bottle devices. Each pill bottle device may be configured to actively or passively transmit data that identifies an associated medication associated with the pill bottle device.

A look-up table may identify various pairs of medications that are to trigger locking of the pill bottle device. In some instances, mere identification of the pair on the table may indicate that the pill bottle device is to lock. In some instances, an additional variable associated with a given medication pair indicates whether the pill bottle device is to lock in response to detecting co-location of the medications.

Upon detecting data from another pill bottle device that identifies another medication, the pill bottle device can use a local or remote look-up table to determine whether the medication and other medication are associated in manner to trigger locking of the pill bottle device. More specifically, the pill bottle device can transmit an identification of the medication and the other medication to the remote server (e.g., via the controller device) and receive an indication as to whether the pill bottle device is to lock. In response to detecting a positive indication, the locking mechanism can engage to thereby prevent access to the medication.

Further, the remote server can transmit a communication to a physician device or a pharmacist device that identifies the medication, other medication and patient. Upon receiving an instruction to unlock the pill bottle device, the remote server can transmit an instruction communication that relays the instruction, such that the pill bottle device begins operating the locking mechanism in accordance with the dosing schedule.

Example 4—Pill Bottle with Medication-Access Function. A pill bottle device can be configured similar to that from Example 3. However, the condition set for the device can be configured to be satisfied upon detecting predefined survey-response results. For example, the medication contained in the device may include a medication prescribed for a mental illness (e.g., depression, schizophrenia, bipolar disorders) or a medication that produces a positive symptom.

Electronics of the device can be configured to require that a user have submitted one or more survey responses before the locking mechanism is disengaged. Thus, upon detecting an input corresponding to a request to disengage the locking mechanism, the pill bottle device can request an indication from a remote server as to whether the response(s) have been received. If not, the locking mechanism can remain engaged.

If the response(s) have been received, it can be determined whether the condition is satisfied based on the response(s). For example, the condition may be configured to be satisfied if the response(s) indicate that the patient is depressed by a certain degree, experiencing euphoria by a certain degree, considering hurting him/herself and/or having exhibited a personality change by above a threshold amount. If the condition is satisfied, the locking mechanism can remain engaged and an alert (including a patient identifier and the survey response(s)) can be transmitted to a physician or health care provider (via the remote server).

Example 5—At-Home Diagnostic Kit with Automated-Sample-Analysis Function. A kit can be configured to perform an automatic analysis on a biological sample (e.g., urine or saliva). For example, the kit can be configured to analyze the sample to determine whether it is indicative of an infection, mutation, etc. The kit can be configured to present a result of the analysis at an interface included in the kit or via a connected controller device.

A condition set for the device may be configured to be satisfied when account data for an associated user indicates that a payment for a particular analysis has been received. The payment may be (for example) for a particular analysis, particular time period (e.g., paying for a plurality of analyses within the period), a particular type of analysis, etc.

Upon detecting an input at the kit from a user corresponding to a request to analyze a biological sample, the kit can transmit a request to the remote server (e.g., via the app at the controller device) for an indication as to whether payment has been submitted that corresponds to the requested analysis.

In some instances, the kit can be configured to selectively perform the analysis upon determining that the account data indicates that an appropriate payment has been received. In some instances, the kit can be configured to perform the analysis irrespective of whether the account data indicates that an appropriate payment has been received but to condition a transmission and/or presentation on the result of having received an indication that an appropriate payment has been received.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method comprising:
accessing a usage protocol for a medically related device, the usage protocol identifying one or more operation characteristics that are to control an operation of the medically related device when a particular condition is satisfied, wherein the one or more operation characteristics correspond to a suppressed state of operation of the medically related device as compared to a normal state of operation of the medically related device;
collecting data that corresponds to:
a usage characteristic of the medically related device;
a medically related state of a person;
environmental data indicating a presence or characteristic of an object near the medically related device; or
account data of the person;
determining, based on the collected data, that the particular condition is satisfied;
in response to determining that the particular condition is satisfied:
causing the medically related device to operate in accordance with the one or more operation characteristics and to enter the suppressed state of operation; and
causing an alert to be presented at a user device, the alert including:
an indication that the medically related device is operating in the suppressed state; and
a characterization of the collected data.

2. The method of claim 1, wherein:
the collected data includes the usage characteristic and is indicative of a clock-setting time that initiates a time period for use of the medically related device in the normal state of operation;
determining that the particular condition is satisfied includes determining that at least a predefined threshold amount of time has elapsed since the last clock-setting time; and
the alert further indicates that the medically related device is to remain in the suppressed state until a communication is received from medical professional device that corresponds to an instruction to set a new clock-setting time and resume the normal state of operation.

3. The method of claim 1, wherein:
the collected data includes a quantity associated with a usage of the medically related device within a time period; and
determining that the particular condition is satisfied includes determining that the quantity exceeds a predefined threshold.

4. The method of claim 1, wherein:
the medically related device includes a device that stores a first medication and includes a gating mechanism to selectively restrict access to the first medication;
the collected data includes environmental data and identifies a container of a second medication near the medically related device;
determining that the particular condition is satisfied includes determining, based on a look-up table, that administration of each of the first medication and the second medication may result in undesired target effects; and
the operating in the suppressed state includes locking the medically related device to impede access to the first medication.

5. The method of claim 1, wherein:
the medically related device includes a diagnostic kit configured to analyze a biological sample;
the collected data includes the account data and indicates whether payment has been received for one or more given iterations of performance of the diagnostic kit;
determining that the particular condition is satisfied includes determining that the collected data indicates that the payment has not been received for a particular iteration of performance of the diagnostic kit; and
the operating in the suppressed state includes preventing a result of a particular analysis of a biological sample from being output.

6. The method of claim 1, wherein the collected data corresponds to the medically related state of the person, and wherein the medically related state of the person identifies a medical condition of the person or a clinical measurement for the person.

7. The method of claim 1, wherein the medically related device:
   determines that the particular condition is satisfied;
   causes the medically related device to operate in accordance with the one or more operation characteristics and to enter the suppressed state of operation; and
   causes the alert to be presented at the user device.

8. The method of claim 1, wherein a server:
   determines that the particular condition is satisfied;
   causes the medically related device to operate in accordance with the one or more operation characteristics and to enter the suppressed state of operation; and
   causes the alert to be presented at the user device.

9. The method of claim 1, wherein causing the alert to be presented at the user device includes causing alert data to be transmitted to the user device, the alert data including:
   the characterization of the collected data; and
   an identification of the medically related device or the person; and
   wherein the user device is associated with a physician, pharmacist or medical facility.

10. A computer-program product tangibly embodied in a non-transitory machine-readable storage medium, including instructions configured to cause one or more data processors to perform actions including:
    accessing a usage protocol for a medically related device, the usage protocol identifying one or more operation characteristics that are to control an operation of the medically related device when a particular condition is satisfied, wherein the one or more operation characteristics correspond to a suppressed state of operation of the medically related device as compared to a normal state of operation of the medically related device;
    collecting data that corresponds to:
        a usage characteristic of the medically related device;
        a medically related state of a person;
        environmental data indicating a presence or characteristic of an object near the medically related device; or
        account data of the person;
    determining, based on the collected data, that the particular condition is satisfied;
    in response to determining that the particular condition is satisfied:
        causing the medically related device to operate in accordance with the one or more operation characteristics and to enter the suppressed state of operation; and
        causing an alert to be presented at a user device, the alert including:
            an indication that the medically related device is operating in the suppressed state; and
            a characterization of the collected data.

11. The computer-program product of claim 10, wherein:
    the collected data includes the usage characteristic and is indicative of a clock-setting time that initiates a time period for use of the medically related device in the normal state of operation;
    determining that the particular condition is satisfied includes determining that at least a predefined threshold amount of time has elapsed since the last clock-setting time; and
    the alert further indicates that the medically related device is to remain in the suppressed state until a communication is received from medical professional device that corresponds to an instruction to set a new clock-setting time and resume the normal state of operation.

12. The computer-program product of claim 10, wherein:
    the collected data includes a quantity associated with a usage of the medically related device within a time period; and
    determining that the particular condition is satisfied includes determining that the quantity exceeds a predefined threshold.

13. The computer-program product of claim 10, wherein:
    the medically related device includes a device that stores a first medication and includes a gating mechanism to selectively restrict access to the first medication;
    the collected data includes environmental data and identifies a container of a second medication near the medically related device;
    determining that the particular condition is satisfied includes determining, based on a look-up table, that administration of each of the first medication and the second medication may result in undesired target effects; and
    the operating in the suppressed state includes locking the medically related device to impede access to the first medication.

14. The computer-program product of claim 10, wherein:
    the medically related device includes a diagnostic kit configured to analyze a biological sample;
    the collected data includes the account data and indicates whether payment has been received for one or more given iterations of performance of the diagnostic kit;
    determining that the particular condition is satisfied includes determining that the collected data indicates that the payment has not been received for a particular iteration of performance of the diagnostic kit; and
    the operating in the suppressed state includes preventing a result of a particular analysis of a biological sample from being output.

15. The computer-program product of claim 10, wherein the collected data corresponds to the medically related state of the person, and wherein the medically related state of the person identifies a medical condition of the person or a clinical measurement for the person.

16. The computer-program product of claim 10, wherein the medically related device:
    determines that the particular condition is satisfied;
    causes the medically related device to operate in accordance with the one or more operation characteristics and to enter the suppressed state of operation; and
    causes the alert to be presented at the user device.

17. The computer-program product of claim 10, wherein a server:
    determines that the particular condition is satisfied;
    causes the medically related device to operate in accordance with the one or more operation characteristics and to enter the suppressed state of operation; and
    causes the alert to be presented at the user device.

18. The computer-program product of claim 10, wherein causing the alert to be presented at the user device includes causing alert data to be transmitted to the user device, the alert data including:
    the characterization of the collected data; and
    an identification of the medically related device or the person; and wherein the user device is associated with a physician, pharmacist or medical facility.

19. A system comprising:

one or more data processors; and a non-transitory computer readable storage medium containing instructions which, when executed on the one or more data processors, cause the one or more data processors to perform actions including:
- accessing a usage protocol for a medically related device, the usage protocol identifying one or more operation characteristics that are to control an operation of the medically related device when a particular condition is satisfied, wherein the one or more operation characteristics correspond to a suppressed state of operation of the medically related device as compared to a normal state of operation of the medically related device;
- collecting data that corresponds to:
  - a usage characteristic of the medically related device;
  - a medically related state of a person;
  - environmental data indicating a presence or characteristic of an object near the medically related device; or
  - account data of the person;
- determining, based on the collected data, that the particular condition is satisfied;
- in response to determining that the particular condition is satisfied:
  - causing the medically related device to operate in accordance with the one or more operation characteristics and to enter the suppressed state of operation; and
  - causing an alert to be presented at a user device, the alert including:
    - an indication that the medically related device is operating in the suppressed state; and
    - a characterization of the collected data.

20. The system of claim 19, wherein:

the collected data includes the usage characteristic and is indicative of a clock-setting time that initiates a time period for use of the medically related device in the normal state of operation;

determining that the particular condition is satisfied includes determining that at least a predefined threshold amount of time has elapsed since the last clock-setting time; and the alert further indicates that the medically related device is to remain in the suppressed state until a communication is received from medical professional device that corresponds to an instruction to set a new clock-setting time and resume the normal state of operation.

* * * * *